United States Patent [19]
Lescouzeres et al.

[11] Patent Number: 5,879,630
[45] Date of Patent: Mar. 9, 1999

[54] SEMICONDUCTOR CHEMICAL SENSOR DEVICE AND METHOD OF FORMING A THERMOCOUPLE FOR A SEMICONDUCTOR CHEMICAL SENSOR DEVICE

[75] Inventors: Lionel Lescouzeres; Alexandra Lorenzo; Emmanual Scheid, all of Toulouse, France

[73] Assignee: Motorola, Inc., Schaumburg, Ill.

[21] Appl. No.: 799,729

[22] Filed: Feb. 13, 1997

[30] Foreign Application Priority Data

Mar. 4, 1996 [FR] France ................................. 96 02669

[51] Int. Cl.[6] .................................................. G01N 27/14
[52] U.S. Cl. .................................. 422/82.02; 422/82.01; 422/82.03; 422/95; 422/98; 73/31.05; 338/34
[58] Field of Search ....................... 422/82.01, 82.02, 422/82.03, 98, 95; 73/31.05, 31.06; 338/34

[56] References Cited

U.S. PATENT DOCUMENTS

| | | |
|---|---|---|
| 3,766,444 | 10/1973 | Bosch . |
| 3,932,246 | 1/1976 | Stadler et al. . |
| 4,141,955 | 2/1979 | Obiaya ..................................... 422/95 |
| 4,283,261 | 8/1981 | Maurer et al. . |
| 4,313,338 | 2/1982 | Abe et al. ............................... 73/31.06 |
| 4,325,912 | 4/1982 | Sawa et al. ............................ 422/98 X |
| 5,140,393 | 8/1992 | Hijikihigawa ............................ 357/25 |
| 5,600,174 | 2/1997 | Reay et al. ............................. 257/467 |
| 5,602,324 | 2/1997 | Yanagida et al. ....................... 73/23.2 |

FOREIGN PATENT DOCUMENTS

| | | |
|---|---|---|
| 59-90040 | 5/1984 | Japan . |
| 59-143947 | 8/1984 | Japan . |

OTHER PUBLICATIONS

C. Gladun et al. *Proc. Int. Conf. Thermoelectr. 1992*, 11th, 92–97.

S. Nowak et al. *Proc. SPIE–Int. Soc. Opt. Eng. 1992*, 1783, 315–321.

*Primary Examiner*—Arlen Soderquist
*Attorney, Agent, or Firm*—Robert F. Hightower

[57] ABSTRACT

A semiconductor chemical sensor device (2) comprises a sensitive layer (4) for detecting specific chemicals and a heater for heating the sensitive layer, which is formed by a heater portion (6) of a conductive layer (8) in the semiconductor chemical sensor device (2). The semiconductor chemical sensor device (2) further comprises a thermocouple (12) for detecting the temperature of the sensitive layer (4), the thermocouple comprising a P/N junction (14) formed as part of or adjacent the heater portion (6) of the conductive layer (8) such that a signal developed across the P/N junction (14) is representative of the temperature of the sensitive layer (4).

10 Claims, 4 Drawing Sheets

— 1 —

SEMICONDUCTOR CHEMICAL SENSOR DEVICE AND METHOD OF FORMING A THERMOCOUPLE FOR A SEMICONDUCTOR CHEMICAL SENSOR DEVICE

FIELD OF THE INVENTION

This invention relates to a semiconductor chemical sensor device and method of forming a thermocouple for such a device.

BACKGROUND OF THE INVENTION

A chemical sensor is a device which monitors the concentration of a given chemical species in a liquid or a gas. Chemical sensors are used, for example, to detect unsafe levels of poisonous or explosive gases in the work and home environments.

Chemical sensors formed using hybrid technology, such as for example sensors formed on ceramic substrates, are well known. It is also known to fabricate a semiconductor chemical sensor on a semiconductor substrate. This invention is concerned with semiconductor chemical sensors.

Typically chemical sensors comprise a sensitive layer, which is sensitive to particular chemical species which are to be detected by the sensor. The reaction of the sensitive layer with the chemical species to be detected results in a change in the physical properties of the sensitive layer, e.g. resistivity or surface potential. As the reaction of the sensitive layer is governed by thermodynamic relations, temperature plays an important role in optimising the output of the sensor device, e.g. sensitivity and selectivity. Some sensors comprise a heater for increasing the temperature of the sensitive layer to increase the sensitivity and selectivity of the sensor. Depending on the chemical species to be detected, chemical sensors may need to be heated to quite high temperatures, for example in the range of 250°–650° C.

Since the selectivity of a chemical sensor depends on the temperature to which the sensitive layer is heated, it is therefore desirable that the temperature of the sensitive layer or heater is accurately monitored over a temperature range such as 250°–650° C.

Poly resistors and metallic resistors have been used to monitor the operating temperature in semiconductor chemical sensors, see for example the article by Wan Young Chun, in Sensors and Actuators B, 20 (1994) 139–143. However, such techniques both require significant die space and can only monitor the temperature over a large area of the die. Such techniques therefore lack accuracy.

It is therefore desirable to provide an improved semiconductor chemical sensor device with a temperature detector which does not suffer from the above referenced problems.

SUMMARY OF THE INVENTION

In accordance with the present invention there is provided a semiconductor chemical sensor device having a sensitive layer for detecting specific chemicals and a heater for heating the sensitive layer, the heater being formed by a heater portion of a conductive layer in the semiconductor chemical sensor device, the semiconductor chemical sensor device further comprising a thermocouple for detecting the temperature of the sensitive layer, the thermocouple comprising a P/N junction formed as part of or adjacent the heater portion of the conductive layer such that a signal developed across the P/N junction is representative of the temperature of the sensitive layer.

The present invention provides a chemical sensor device having a small thermocouple for detecting the temperature of the sensitive layer which can be easily integrated into the chemical sensor device. The thermocouple can be positioned in or very close to the heater and can therefore provide more accurate temperature detection which ensures better selectivity and sensitivity of the chemical sensor device.

Since the thermocouple is small, a plurality of thermocouples can be integrated into the chemical sensor device so as to monitor and control the temperature accurately and uniformly over a large die area.

A method of forming a thermocouple for a semiconductor chemical sensor device is also disclosed and claimed.

BRIEF DESCRIPTION OF THE DRAWINGS

Three semiconductor chemical sensor devices in accordance with the present invention and a method of forming a thermocouple for such chemical sensor devices will now be described, with reference to the accompanying drawings in which.

DETAILED DESCRIPTION OF THE DRAWINGS

Figure 1:
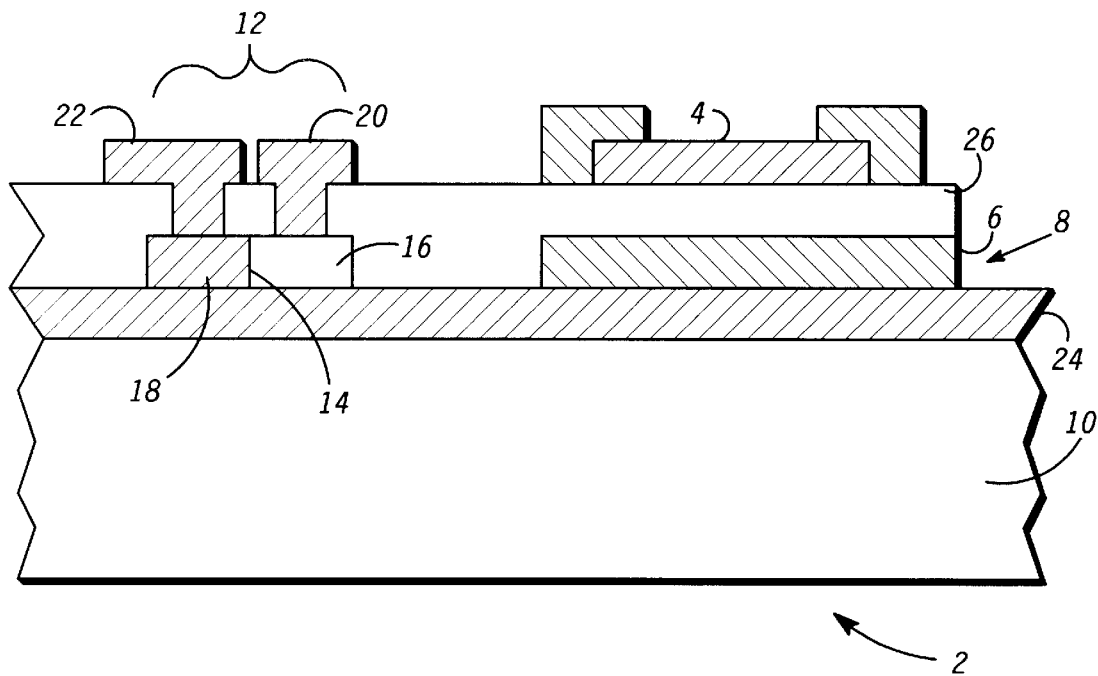
FIG. 1 shows a simplified schematic cross-sectional view of a semiconductor chemical sensor device in accordance with a first embodiment of the present invention.

Referring firstly to FIG. 1, a semiconductor chemical sensor device 2 in accordance with a first embodiment of the present invention comprises a sensitive layer 4 for detecting specific chemicals and a heater for heating the sensitive layer 4. The heater is formed by a heater portion 6 of a conductive layer 8 formed over a semiconductor layer 10. The semiconductor chemical sensor device 2 further comprises a thermocouple 12 for detecting the temperature of the sensitive layer 4, the thermocouple 12 comprising a P/N junction 14 formed adjacent the heater portion 6 of the conductive layer 8. A signal is developed across the P/N junction 14, which signal is representative of the temperature at the P/N junction 14 according to the Seebeck effect and hence is representative of the temperature of the sensitive layer 4.

The thermocouple 12 comprises a portion 16 of the conductive layer 8, adjacent the heater portion 6, and a conductive region 18 formed in the conductive layer 8, the conductive region 18 being formed of a conductive material having a different conductivity type to that of the conductive layer 8. A junction between the portion 16 of the conductive layer 8 and the conductive region 18 forms the P/N junction 14 of the thermocouple 12. A first contact 20 extends to the portion 16 of conductive layer 8 and a second contact 22 extends to the conductive region 18. A voltage signal is developed across the first 20 and second 22 contacts which corresponds to the signal across the PIN junction 14 and hence the temperature of the sensitive layer 4.

Preferably, the conductive layer 8 is formed from N+ doped polysilicon formed on a first insulating layer 24, such as a silicon oxide layer, which insulating layer is formed on the semiconductor layer 10. The semiconductor layer 10 may be a silicon substrate. The conductive region 18 is preferably P+ doped polysilicon whereby a junction of poly P+ and poly N+ forms the P/N junction 14. The N+ doped polysilicon and P+ doped polysilicon when heavily doped function as metals. Such a junction produces a voltage signal as a function of temperature by virtue of the Seebeck effect.

A second insulating layer 26, such as a TEOS layer or a silicon oxide layer, provides insulation between the sensitive layer 4 and the conductive layer 8. The sensitive layer 4 is formed on the second insulating layer 26 and may be formed from a gold layer, or a gold-palladium alloy layer for sensing hydride gases. For a carbon monoxide sensor device, the sensitive layer 4 may comprise a tin oxide layer. The type of sensitive material which is used to form the sensitive layer 4 may vary from metals to doped/compound materials and depends on the applications and the type of chemicals the semiconductor chemical sensor device 2 is to detect.

In the first embodiment, the thermocouple 12 is formed adjacent the heater portion 6 of the conductive layer 8. The thermocouple may, in addition or alternatively, be formed as part of the heater as is shown in FIG. 2.

Figure 2:
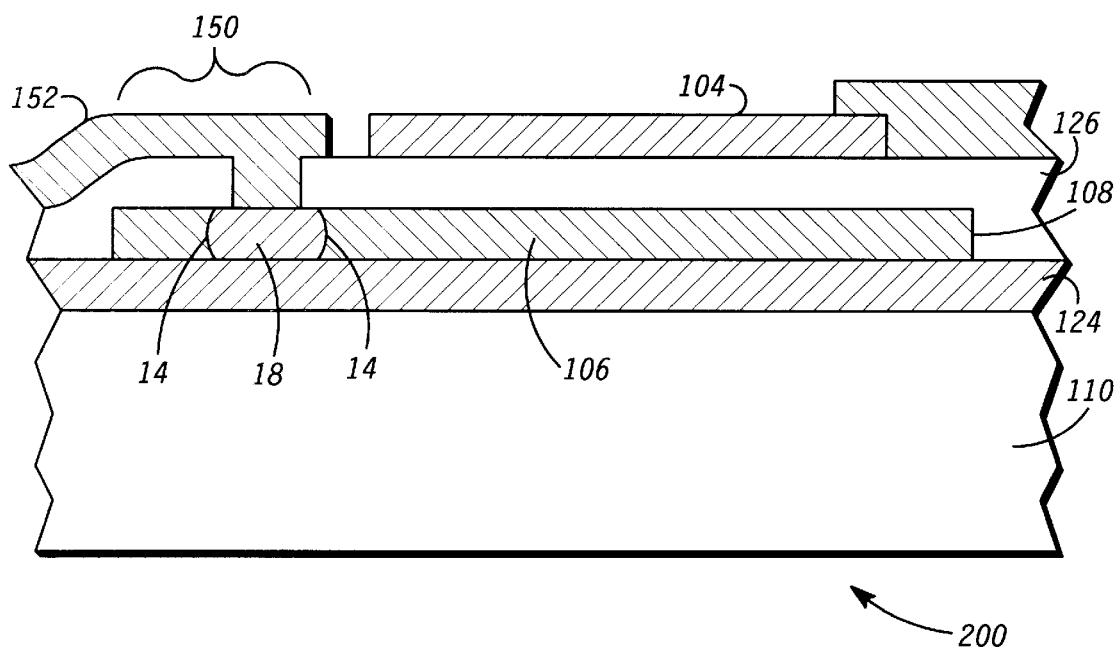
FIG. 2 shows a simplified schematic cross-sectional view of a semiconductor chemical sensor device in accordance with a second embodiment of the present invention.
Figure 3:
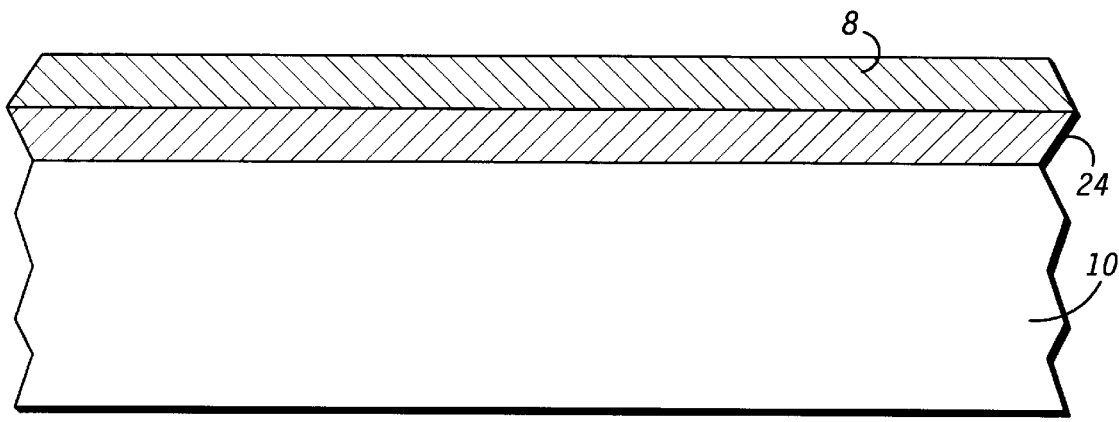
FIGS. 3–6 show simplified schematic cross-sectional views of the semiconductor chemical sensor device of FIG. 1 during different stages of fabrication and according to the present invention.

Referring now to FIG. 2, a semiconductor chemical sensor device 200 in accordance with a second embodiment of the present invention is shown. Like features to those of FIG. 1 are referenced by the same reference numeral plus one hundred.

The semiconductor chemical sensor device 200 comprises a sensitive layer 104 for detecting specific chemicals and a heater for heating the sensitive layer 104. The heater is formed by a heater portion 106 of a conductive layer 108 formed over a semiconductor layer 110. The semiconductor chemical sensor device 200 further comprises a thermocouple 150 for detecting the temperature of the sensitive layer 104 and comprising a P/N junction 114 formed in the heater portion 106 of the conductive layer 108. A signal representative of the temperature of the P/N junction 114 and hence the sensitive layer 4 is developed across the P/N junction 114.

The thermocouple 150 comprises a conductive region 118 formed in the heater portion 106 of the conductive layer 108. The conductive region 118 is formed of a conductive material of different conductivity type to that of the conductive layer 108. A contact 152 extends to the conductive region 118. A voltage signal is developed across the contact 152 and a contact (not shown) to the heater portion 106 which corresponds to the signal across the P/N junction 114 of the thermocouple 150. The voltage signal at the contact 152 therefore represents the temperature of the sensitive layer 104.

As in the first embodiment, preferably, the conductive layer 108 is formed from N+ doped polysilicon formed on a first insulating layer 124, such as a silicon oxide layer, formed on the semiconductor layer 110. The conductive region 118 is preferably P+ doped polysilicon whereby a junction of poly P+ and poly N+ forms the P/N junction 114. Such a junction produces a voltage signal as a function of temperature by virtue of the Seebeck effect.

A second insulating layer 126, such as a TEOS layer or a silicon oxide layer, provides insulation between the sensitive layer 104 and the conductive layer 108. The material from which the sensitive layer 104 is formed depends on the applications and the type of chemicals the semiconductor chemical sensor device 200 is to detect.

A method of forming a thermocouple for a semiconductor chemical sensor device in accordance with the invention will now be described with reference to forming the thermocouple 12 of the semiconductor chemical sensor 2 in accordance with the first embodiment of the present invention and with reference to FIGS. 1, 3–7.

A semiconductor layer 10, preferably a silicon substrate, is provided and a silicon oxide (thermal oxide) first insulating layer 24 is formed over the silicon substrate 10. A conductive layer 8, preferably comprising a N+ doped polysilicon layer, is formed over the silicon oxide first insulating layer 24 (see FIG. 3). These are the same steps which are used to form the heater of the semiconductor chemical sensor device.

Figure 4:
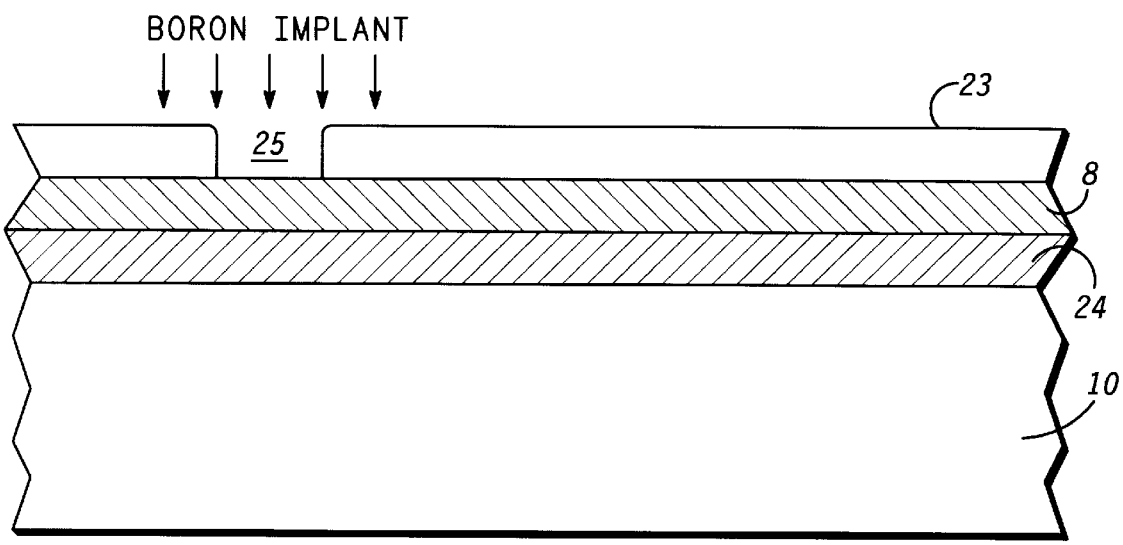
Figure 5:
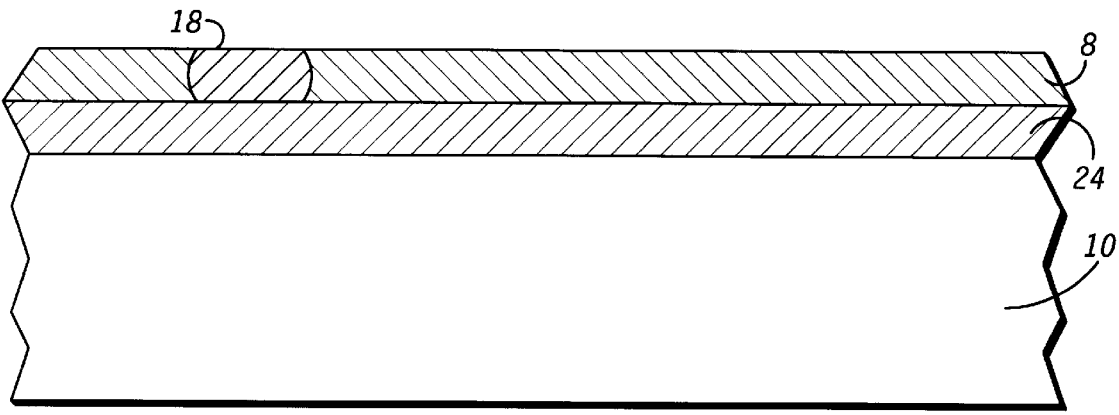
Figure 6:
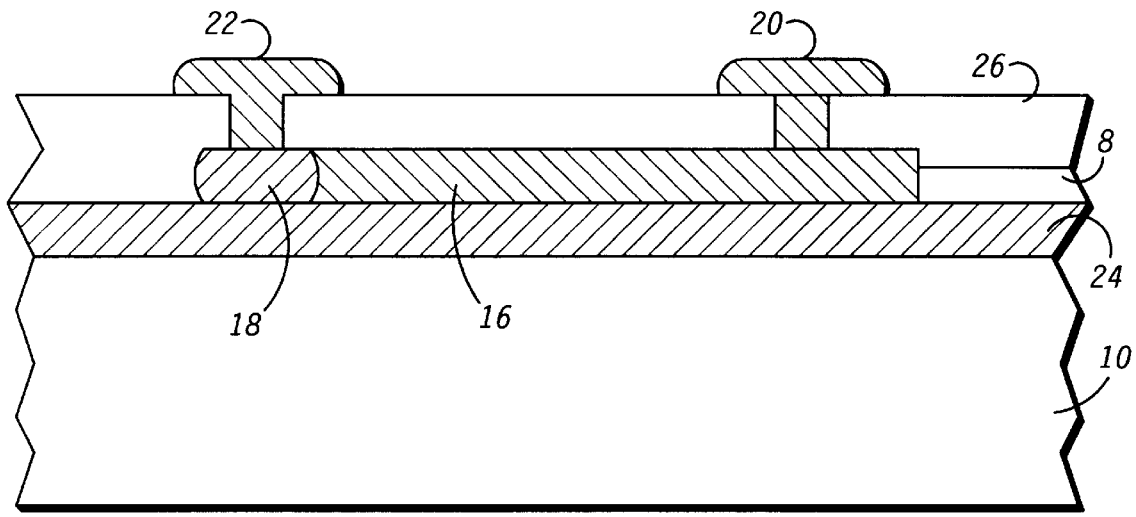
Figure 7:
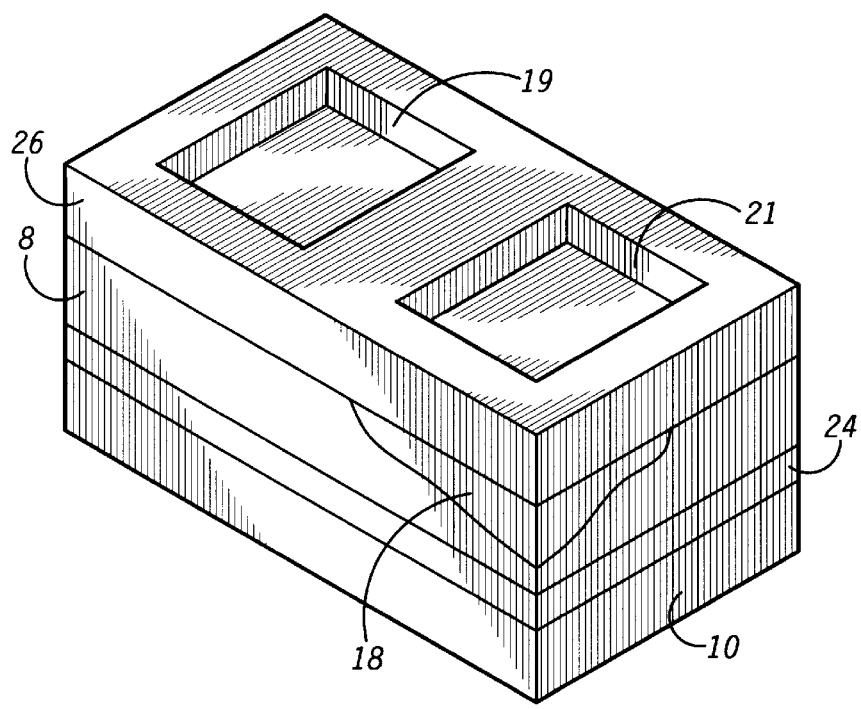
FIG. 7 shows a simplified schematic plan view of the thermocouple of the semiconductor chemical sensor device of FIG. 1 before metallization.

A mask 23, such as photoresist ,is formed over the conductive layer 8 which is then patterned and etched to provide an opening 25 through the photoresist 23 to the conductive layer 8 (see FIG. 4). Boron, or any other P species, is then implanted at quite a high dose into the conductive layer 8 through the opening 25 to dope the N+ polysilicon conductive layer 8 with P dopant. The photoresist 23 is then removed. Thus, a conductive region 18 is formed in the conductive layer 8 having a different conductivity type to that of the conductive layer 8 (FIG. 5); that is, poly P+ versus poly N+ respectively.

The conductive layer 8 is then patterned and etched to form the heater portion 6 (not shown in FIG. 6) and portion 16 of the thermocouple 12.

A second insulating layer 26 is then formed over the conductive layer 8 and insulating layer 24. The second insulating layer 26 is patterned and etched to form contact openings to the conductive region 18 and to the conductive layer 8. Metallization is then formed in the contact openings to form the first 20 and second 22 contacts. The contact openings 19, 21 can be seen more clearly in FIG. 7 which shows a perspective view of FIG. 6 before metallization.

The heater of the semiconductor chemical sensor device in accordance with the invention is formed from the conductive layer 8. Thus, it will be appreciated from the above that the initial steps of forming a conductive region 18 in a conductive layer 8 correspond to the steps of forming the heater. Since only additional photo and implant steps are required to form the thermocouple 12, few steps are required to integrate a thermocouple in accordance with the present invention in a semiconductor chemical sensor device.

It will be appreciated that substantially the same method can be used to form the thermocouple 150 of the second embodiment. The patterning and etching steps of the conductive layer 108 will be slightly different for the second embodiment, since the thermocouple 150 is part of the heater itself.

Each of the semiconductor chemical sensor devices in accordance with first and second embodiments of the present invention has so far been described as comprising one thermocouple. However, this is for illustrative purposes only. A chemical sensor device in accordance with the invention may comprise one or more thermocouples. That is, a chemical sensor device in accordance with the invention may comprises one or more of the thermocouples 12 in accordance with the first embodiment or one or more of the thermocouples 150 in accordance with the second embodiment. Furthermore, a chemical sensor device in accordance with the invention may comprise at least one first and at least one second different thermocouples; the first thermocouple being formed as part of the heater and the second thermocouple being formed adjacent the heater.

Figure 8:
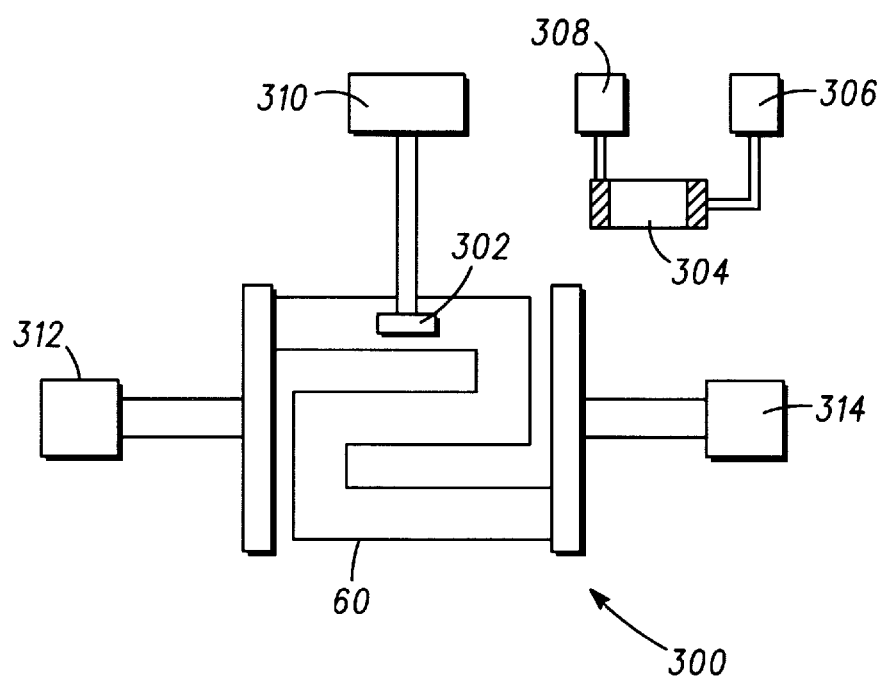
FIG. 8 shows a simplified schematic plan view of part of a semiconductor chemical sensor device in accordance with a third embodiment of the present invention.

Another possible combination is shown in FIG. 8, which shows a schematic top plan view of part of a semiconductor chemical sensor device 300 in accordance with a third embodiment of the invention is shown in FIG. 8.

The chemical sensor device 300 comprises a heater 60, formed from a conductive layer such as N+ doped polysilicon, having a first thermocouple 302 as part of the heater and a second thermocouple 304 remote from the heater, for example at the edge of the semiconductor chemical sensor device die. The first thermocouple 302 corresponds to thermocouple 150 described above and second thermocouple 304 corresponds to the thermocouple 12 described above. Contact 310 is connected to the P+ conductive region of the first thermocouple 302 which is formed in the heater. Contacts 306, 308 are connected to the P+ conductive region and a portion of N+ conductive layer of the second thermocouple 304. Contacts 312 and 314 are the heater contacts.

From the voltage signals generated by thermocouples 302 and 304, the temperature difference between the two regions of the semiconductor chemical sensor device can be determined and also the temperature at the center of the heater.

Preferably, the second thermocouple 304 is at the edge of the die where the silicon is at its maximum thickness. In such an arrangement, the second thermocouple 304 is at a position where the temperature is approximately the same as the temperature of the packaging of the chemical sensor device. Thus, the temperature measured by the second thermocouple 304 substantially corresponds to the ambient external temperature. Such an arrangement can be used to provide immunity against lot to lot variations due to variations in poly resistivity. A small change in resistance will produce a measurable change in temperature. This can be detected by looking at the difference in temperature between the first and second thermocouples for each lot.

Thus, having two or more thermocouples in the semiconductor chemical sensor device, enables the temperature to be monitored and controlled more uniformly and more accurately.

Having two thermocouples within the heater is particularly useful since the temperature across the heater may not be uniform. The temperature of the heater can therefore be monitored at different points and controlled accordingly.

The thermocouple in accordance with the present invention comprises a P/N junction integrated adjacent and/or as part of the heater. Such a thermocouple has very small dimensions, about 30–50 microns, compared to the prior art poly resistors and so ensures good spatial resolution on the die. The small size of the thermocouple means that a plurality of thermocouples may be integrated throughout the semiconductor chemical sensor device, ensuring accurate temperature sensing.

When the heater is formed from a poly conductive layer, the thermocouple can be integrated as part of the heater. In this case, the P/N junction is formed between the heater itself and a conductive region implanted into the heater.

We claim:

1. A semiconductor chemical sensor device having a sensitive layer for detecting chemicals and a heater for heating the sensitive layer, the heater being formed by a heater portion of a polysilicon conductive layer in the semiconductor chemical sensor device, the semiconductor chemical sensor device further comprising a first thermocouple for detecting the temperature of the sensitive layer, the first thermocouple comprising a P/N junction such that a signal developed across the P/N junction is representative of the temperature of the sensitive layer, the P/N junction formed as one of a part of the heater portion of the polysilicon conductive layer or a part of the polysilicon conductive layer adjacent the heater portion of the polysilicon conductive layer.

2. A semiconductor chemical sensor device according to claim 1 wherein the polysilicon conductive layer is formed from a polysilicon material having a first type of conductivity and the first thermocouple comprises a conductive region formed in the polysilicon conductive layer and formed from polysilicon having a second type of conductivity, the conductive region having a first contact extending thereto, the P/N junction of the first thermocouple comprising a junction between the conductive region and the polysilicon conductive layer, and wherein a voltage signal developed at the first contact is representative of the temperature of the sensitive layer.

3. A semiconductor chemical sensor device according to claim 2 wherein the conductive region is formed in the heater portion of the polysilicon conductive layer.

4. A semiconductor chemical sensor device according to claim 3 wherein the polysilicon conductive layer is formed from N+ doped polysilicon and the conductive region is formed from P+ doped polysilicon.

5. A semiconductor chemical sensor device according to claim 3 further comprising a second thermocouple for detecting the temperature of the sensitive layer, the second thermocouple comprising a P/N junction formed adjacent the heater portion of the polysilicon conductive layer such that a signal developed across the P/N junction is representative of the temperature of the sensitive layer.

6. A semiconductor chemical sensor device according to claim 5 wherein the second thermocouple comprises:

a conductive region formed in the polysilicon conductive layer adjacent the heater portion and formed from polysilicon having a second type of conductivity, the conductive region having a first contact extending thereto; and a portion of the polysilicon conductive layer, adjacent the conductive region and adjacent the heater portion of the polysilicon conductive layer, having a second contact extending thereto, the P/N junction of the second thermocouple comprising a junction between the conductive region and the portion of the polysilicon conductive layer, wherein a voltage signal developed across the first and second contacts is representative of the temperature of the sensitive layer.

7. A semiconductor chemical sensor device according to claim 6 wherein the polysilicon conductive layer is formed from N+ doped polysilicon and the conductive regions of the first and second thermocouples are formed from P+ doped polysilicon.

8. A semiconductor chemical sensor device according to claim 1 wherein the polysilicon conductive layer is formed from a polysilicon material having a first type of conductivity and the first thermocouple comprises:

a conductive region formed in the polysilicon conductive layer adjacent the heater portion and formed from polysilicon having a second type of conductivity, the conductive region having a first contact extending thereto; and a portion of the polysilicon conductive layer, adjacent the conductive region and adjacent the heater portion, having a second contact extending thereto, the P/N junction of the first thermocouple comprising a junction between the conductive region and the portion of the polysilicon conductive layer, wherein a voltage signal developed across the first and second contacts is representative of the temperature of the sensitive layer.

9. A semiconductor chemical sensor device according to claim 8 wherein the polysilicon conductive layer is formed from N+ doped polysilicon and the conductive region is formed from P+ doped polysilicon.

10. A semiconductor chemical sensor device having a sensitive layer for detecting chemicals and a heater for heating the sensitive layer, the heater being formed by a heater portion of a polysilicon conductive layer in the semiconductor chemical sensor device, the semiconductor chemical sensor device further comprising:

a first thermocouple for detecting the temperature of the sensitive layer, the first thermocouple comprising a P/N junction formed as part of or adjacent the heater portion of the polysilicon conductive layer such that a signal developed across the P/N junction is representative of the temperature of the sensitive layer; and a second thermocouple for detecting the temperature of a region of the semiconductor chemical sensor device remote from the heater, the second thermocouple comprising a P/N junction formed in a conductive layer such that a signal developed across the P/N junction is representative of the temperature of the region of the semiconductor chemical sensor device.

* * * * *